United States Patent [19]

Filan et al.

[11] 4,201,775

[45] May 6, 1980

[54] BIS[TRIETHYLPHOSPHINE)AURIO]SULFONIUM SUGARS

[75] Inventors: John J. Filan, Philadelphia, Pa.; Walter W. Holl, Cinnaminson, N.J.; George R. Wellman, Warminster, Pa.

[73] Assignee: SmithKline Corporation, Philadelphia, Pa.

[21] Appl. No.: 23,364

[22] Filed: Mar. 23, 1979

[51] Int. Cl.² .................... A61K 31/70; C07H 23/00
[52] U.S. Cl. .................... 424/180; 536/121; 536/4; 536/122
[58] Field of Search .................... 536/121, 122, 4; 424/180

[56] References Cited

U.S. PATENT DOCUMENTS

| 3,635,945 | 1/1972 | Nemeth et al. | 424/180 |
|---|---|---|---|
| 4,096,248 | 1/1978 | Lantos | 536/121 |
| 4,096,249 | 6/1978 | Lantos | 536/121 |
| 4,115,642 | 9/1978 | Hill et al. | 536/121 |
| 4,124,759 | 11/1978 | Hill et al. | 536/121 |
| 4,125,710 | 11/1978 | Hill et al. | 536/121 |

*Primary Examiner*—Johnnie R. Brown
*Assistant Examiner*—Blondel Hazel
*Attorney, Agent, or Firm*—William H. Edgerton

[57] ABSTRACT

A new series of gold containing sugars having antiarthritic activity are characterized by the presence of a bis[(triethylphosphine)aurio]sulfonium salt moiety at the 1-position of the glucopyranoside. The compounds are prepared by reacting a 1-S-triethylphosphinegold-1-thio-glucopyranoside with a triethylphosphinegold halide.

5 Claims, No Drawings

BIS[TRIETHYLPHOSPHINE)AURIO]SULFONIUM SUGARS

This invention relates to a new series of organic gold compounds having anti-arthritic activity whose structures are characterized by having a bis [(triethylphosphine)aurio]sulfonium halide substituent at the 1-position of a glucopyranoside.

It is known in the art that certain gold containing glycopyranosides have anti-arthritic activity using oral administration. These compounds have a triethylphosphine-goldthio [$(C_2H_5)_3$P-Au-S-] substituent at the 1-position. (U.S. Pat. Nos. 3,635,945; 4,096,248; or 4,096,249). There is no indication in this art that sugar compounds containing a bis[(triethylphosphine)aurio]sulfonium halide moiety in their structures could be easily prepared and would have anti-arthritic activity.

The compounds of this invention are, to the best of our present knowledge, illustrated by the following structural formula:

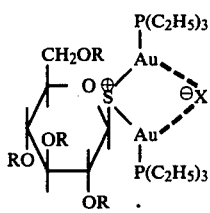

in which:
X is halide such as iodide, bromide or chloride; and
R is acetyl, methylsulfonyl, lower alkyl of 1–3 carbon atoms or N-methylcarbamoyl.

A subgeneric group of this invention comprises compounds of formula I in which R is acetyl and within that group the species of most interest is the chloride (X is $Cl^{\ominus}$).

The compounds of this invention are prepared most conveniently by reacting substantially equimolar quantities of the triethylphosphinegold (I)-1-thio-β-D-glucopyranoside and a triethylphosphinegold (I) halide in an inert solvent in which the reactants are soluble such as ethanol, chloroform, methanol/methylene chloride, toluene, xylene, benzene or tetrahydrofuran most conveniently at room temperature. The reaction is very facile, almost instantaneous, so the temperature and time of reaction may vary widely but with little advantage over dissolving the reactants in an organic solvent at ambient temperature for up to 1–2 hours. Of course the reaction is allowed to proceed to completion for as long as necessary under the selected reactive conditions.

The sulfonium salt product is isolated by methods known to the art but most appropriately by evaporating the reaction solvent. The purity of the product depends largely on the purity of the starting materials.

The anti-arthritic activity of the compounds of this invention is demonstrated in the adjuvant induced arthritis procedure whose protocol is as follows:

In this test procedure, adjuvant arthritis in rats is produced by a single intradermal injection of 0.75 mg of Mycobacterium butyricum suspended in white paraffin oil into the left hindpaw footpad. The injected paw becomes inflamed (increased volume) and reaches maximal size within three to five days (primary lesion). The animals exhibit a decrease in body weight gain during the initial period. The adjuvant arthritis (secondary lesion) occurs after approximately ten days and is characterized by inflammation of the non-injected right hind leg, decrease in body weight, and further increase in the volume of the injected left hind leg. Test compounds are administered daily, beginning on the day of the adjuvant injection, for 17 days thereafter, exclusive of days 4, 5, 11 and 12. Anti-arthritic activity is shown by the ability to inhibit the development of either primary or secondary lesions of adjuvant arthritis. Auranofin which is a clinically effective anti-arthritic is active in test procedures at doses of from 10–20 mg/kg orally.

An example of this invention (2,3,4,6-tetra-O-acetyl-1-β-D-glucopyranosyl)bis [triethylphosphine)aurio]sulfonium chloride whose structure is represented by formula I in which R is acetyl and X is chloride, in this test showed activity at 200 mg/kg/day orally with a survival rate of 62% and with little change of survival rate. Some gastro-intestinal upset was observed.

The compounds of this invention are administered in conventional dosage forms prepared by combining a compound of formula I in a nontoxic amount sufficient to produce anti-arthritic activity with standard pharmaceutical carriers according to conventional procedures. These procedures may involve mixing, granulating and compressing or dissolving the ingredients as appropriate to the desired preparation. The resulting pharmaceutical compositions are also objects of this invention. Oral dosage forms are preferred.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampule or nonaqueous liquid suspension.

Preferably, each dosage unit will contain the active ingredient in an amount of from about 1 mg to about 10 mg.

The method of producing anti-arthritic activity by administering internally to an animal in need of treatment a compound of formula I is also an object of this invention. The compound of formula I is administered in an amount sufficient to produce anti-arthritic activity but have no limiting side effects. The route of administration is preferably oral. The daily dosage regimen will be preferably from about 1 mg to about 12 mg most often in one or two oral doses daily. When the method is carried out as described above, anti-arthritic activity is produced in a subject with arthritic symptoms, for example in humans or in domestic animals such as dogs.

One skilled in the art will recognize that in determining the amounts of active ingredient in the claimed compositions and used in the claimed methods, the activity of the chemical ingredient in the test protocol compared with auranofin as well as the size and condition of the host animal must be considered. The amounts given above are calculated for the average human subject.

The following examples are designed to illustrate this invention. Temperatures are in degrees Centigrade.

EXAMPLE 1

A mixture of 9.6 g of triethylphosphinegold 2,3,4,6-tetra-O-acetyl-1-thio-β-D-glycopyranoside and 5.0 g of triethylphosphinegold chloride in 50 ml of toluene was stirred overnight at room temperature. The solvent was removed in vacuo to give 14.6 g of (2,3,4,6-tetra-O-acetyl-1-β-D-glycopyranosyl)bis [(triethylphosphine)aurio]sulfonium chloride; m.p. 81.5° $[\alpha]_o^{25°}$ −53.2 (c=1 in methanol), mass spectrum shows a M+ion at 993. MNR and IR spectra satisfactory.

Anal. Theoretical; C, 30.35; H, 4.79; P, 6.02; Au, 38.28; Cl, 3.45. Found: C, 30.74; H, 4.96; P, 5.99; Au, 38.35; Cl, 3.45.

Another run gave a similar product with a melting point of 82.6°.

Substituting triethylphosphinegold bromide or iodide gives the corresponding halide of the desired product. Other anions which are pharmaceutically acceptable may also be present in place of the halide ion.

EXAMPLE 2

A mixture of 1.6 g of triethylphosphinegold (I) 2,3,4,6-tetra-O-methylsulfonyl-1-β-D-glucopyranoside (U.S. Pat. No. 4,096,248) and 0.5 g of triethylphosphinegold chloride in tetrahydrofuran is allowed to stand at room temperature for two hours. The solvent is removed by evaporation in vacuo to give (2,3,4,6-tetra-O-methylsulfonyl-1-β-D-gluco-pyranosyl)bis [(triethylphosphine)aurio] sulfonium chloride.

EXAMPLE 3

A mixture of 1.2 g of triethylphosphinegold (I) 2,3,4,6-tetra-O-methyl-1-β-D-glucopyranoside (U.S. Pat. No. 4,096,247) and one mole equivalent of triethylphosphinegold chloride in xylene is prepared and evaporated in vacuo to remove the solvent leaving (2,3,4,6-tetra-O-methyl-1-β-D-gluco-pyranosyl)bis [(triethylphosphine)aurio]sulfonium chloride.

EXAMPLE 4

A mixture of 500 mg of triethylphosphinegold (I) 2,3,4,6-tetra-O-(N-methylcarbamyl)-1-β-D-glucopyranoside (U.S. Pat. No. 4,096,249) and one mole equivalent of triethylphosphinegold chloride in benzene is prepared and evaporated in vacuo to leave [2,3,4,6-tetra-O-(N-methylcarbamyl)-1-β-D-glucopyranosyl]bis [(triethylphosphine)aurio]sulfonium chloride.

EXAMPLE 5

| Ingredients | Amounts |
|---|---|
| (2,3,4,6-tetra-O-acetyl-1-β-D-glucopyranosyl) bis[(triethylphosphine)aurio]sulfonium chloride | 10 mg. |
| Magnesium stearate | 5 mg. |
| Lactose | 135 mg. |

The above ingredients are mixed, screened and filled into a hard gelatin capsule which is administered orally to a human subject having the symptoms of arthritis from 1–4 times daily.

What is claimed is:

1. A chemical compound of the formula:

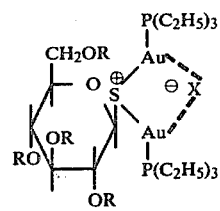

in which:

X is iodide, bromide or chloride; and

R is acetyl, methylsulfonyl, lower alkyl of 1–3 carbon atoms or N,N-dimethylcarbamyl.

2. The compound of claim 1 in which X is chloride and R is acetyl.

3. The compound of claim 1 in which X is chloride and R is methyl.

4. A method of producing anti-arthritic activity which comprises administering orally to a subject in need of anti-arthritic treatment an effective nontoxic quantity of a compound of claims 1, 2 or 3.

5. A pharmaceutical composition having antiarthritic activity, in dosage unit form, comprising a pharmaceutical carrier and an effective nontoxic quantity of a compound of claims 1, 2 or 3.

* * * * *